United States Patent [19]

Matsuo et al.

[11] Patent Number: 4,489,728
[45] Date of Patent: Dec. 25, 1984

[54] DEVICE FOR DIAGNOSING BODY CAVITY INTERIOR WITH SUPERSONIC WAVES

[75] Inventors: Kazumasa Matsuo, Tama; Akio Nakada, Hachioji, both of Japan

[73] Assignee: Olympus Optical Co., Ltd., Tokyo, Japan

[21] Appl. No.: 358,584

[22] Filed: Mar. 16, 1982

[30] Foreign Application Priority Data

| Mar. 22, 1981 | [JP] | Japan | 56-40819 |
| Mar. 22, 1981 | [JP] | Japan | 56-40820 |
| Mar. 22, 1981 | [JP] | Japan | 56-40822 |
| Mar. 22, 1981 | [JP] | Japan | 56-40823 |

[51] Int. Cl.³ .............................. A61B 10/00
[52] U.S. Cl. ........................... 128/660; 128/4
[58] Field of Search .................. 128/660, 4, 6

[56] References Cited

U.S. PATENT DOCUMENTS

| 3,779,234 | 12/1973 | Eggleton et al. | 128/660 |
| 4,149,419 | 4/1979 | Connell, Jr. et al. | 128/660 X |
| 4,374,525 | 2/1983 | Baba | 128/660 |
| 4,391,282 | 7/1983 | Ando et al. | 128/660 |

FOREIGN PATENT DOCUMENTS

| 55-94230 | 7/1980 | Japan . |
| 55-94231 | 7/1980 | Japan . |
| 55-96130 | 7/1980 | Japan . |
| 55-96132 | 7/1980 | Japan . |

*Primary Examiner*—Kyle L. Howell
*Assistant Examiner*—Francis J. Jaworski
*Attorney, Agent, or Firm*—Armstrong, Nikaido, Marmelstein & Kubovcik

[57] ABSTRACT

A device for diagnosing a body cavity interior with supersonic waves is disclosed wherein a supersonic wave tip is inserted into a body cavity to transmit and receive supersonic waves to diagnose internal organs with the supersonic waves and an endoscope to observe the body cavity interior are combined with each other. In such diagnosing device there is provided, a driving means for driving a supersonic wave oscillator or scanning mirror provided within a supersonic probe tip. A grip which is small and light and angled in the forward direction is provided. The disposition of the driving shaft, signal cord and light guide cables are such that they do not obstruct the operation of the diagnosing device.

7 Claims, 16 Drawing Figures

DEVICE FOR DIAGNOSING BODY CAVITY INTERIOR WITH SUPERSONIC WAVES

BACKGROUND OF THE INVENTION

This invention relates to a device for diagnosing a body cavity interior with supersonic waves wherein an endoscope is incorporated in a supersonic wave probe body to contact and diagnose an internal organ while being viewed.

A means of obtaining information on an object by utilizing supersonic waves has recently come to be extensively used even in the medical field. For example, when supersonic wave pulses are projected into a body from the body surface, the above mentioned projected supersonic waves will be propagated and will be reflected by a discontinuous boundary surface of an acoustic impedance represented by the product of the density of the medium and the velocity of the sound, therefore the above mentioned reflected supersonic wave pulses will be received and such acoustic information as the reflecting intensity will be utilized for the diagnosis.

As compared with an X-ray device, such supersonic wave diagnosing device has more advantages in that information on a biotic soft structure can be easily obtained without using a molding agent, that a biotic structure is not destroyed by radioactive rays and that the device is easier to handle and is less dangerous. Further, recently the technique on supersonic waves has progressed and the obtained information has been improved in quality and quantity so much that the supersonic wave diagnosing device is becoming increasingly popular as a clinical diagnosing device.

Against the above mentioned diagnosis wherein supersonic wave pulses are transmitted and received from the surface of a body, the body cavity interior supersonic wave diagnosing method wherein supersonic wave pulses are transmitted and received from a position near a biotic internal organ within a body cavity has more advantages in that it is possible to obtain analyzable information at a high frequency and that information being of a high precision and that the diagnosis is not influenced by a hypodermic fat layer, or the like, interposed between objects and therefore will be used more in the future. Such supersonic wave diagnosing device to be used as inserted into a body cavity is generally and conveniently used by incorporating an endoscope as an optically observing means.

Among the prior arts of such body cavity interior supersonic wave diagnosing devices wherein a supersonic wave probe inserted into a body cavity for transmitting and receiving supersonic waves to and from an internal organ and an endoscope are combined with each other, there are disclosed a "Probe for Inspecting a Body Cavity Interior" mentioned in the Gazette of Japanese Patent Laid Open No. 94230/1980, a "Body Cavity Interior Inspecting Probe" mentioned in the Gazette of Japanese Patent Laid Open No. 94231/1980, a "Supersonic Wave Probe" mentioned in the Gazette of Japanese Patent Laid Open No. 96130/1980 and an "Endoscope" mentioned in the Gazette of Japanese Patent Laid Open No. 96132/1980. However, each of the body cavity interior supersonic wave diagnosing devices of the the above mentioned prior arts disclose nothing of the arrangements having a driving cable for the supersonic wave oscillator or scanning mirror, a signal cable for of the supersonic wave oscillator and a light guide cable connected with the light source means to transmit the illuminating light to the endoscope.

BRIEF SUMMARY OF THE INVENTION

An object of the present invention is to provide a device for diagnosing a body cavity interior with supersonic waves wherein it contains a grip on the hand side of an inserted part which is provided at the tip with a supersonic wave probe tip for transmitting and receiving supersonic waves and is provided internally with an endoscope so as to be inserted into a body cavity. The device is made small and light and is connected through a flexible cable with a driving means formed separately from the above mentioned grip to drive a supersonic wave oscillator or scanning mirror within the supersonic wave probe tip. Thus the operability of such operations is improved such as the inserting the above mentioned inserted part into the body cavity and the contacting the supersonic wave probe tip with an internal organ and, in operation, the grip may be gripped with one hand by the operator thus leaving the other hand free to shape the posture of the patient and press the body wall.

Another object of the present invention is to provide a body cavity interior supersonic wave diagnosing device wherein the direction of connecting the cable to the grip and the direction of connecting the light guide cable to the endoscope are made to coincide with each other in the same lateral direction with respect to the axial direction of the inserted part. Thus, the cable connected to the above mentioned grip and the light guide cable connected to the endoscope is not in the way of such supersonic wave diagnosing operations of inserting the inserted part into the body cavity and contacting the supersonic wave probe tip with the internal organ while being observed with the endoscope.

Further, another object of the present invention is to provide a body cavity interior supersonic wave diagnosing device wherein wires for electric signals of a flexible rotary driving shaft and oscillator for scanning supersonic waves are internally provided in a flexible cable so that the grip of the inserted part may be flexibly connected with the driving means through one cable. Thus, the operation of inserting the inserted part and supersonic wave probe tip into the body cavity and contacting the tip with the internal organ is made easy.

Another object of the present invention is to provide a body cavity interior supersonic wave diagnosing device wherein a rotary driving shaft joint for removably connecting electric signal cords of a flexible rotary driving shaft for scanning supersonic waves and of an oscillator and an electric connecting part are provided respectively in a driving means and flexible cable and a grip so that the flexible rotary driving shaft and electric signal cords may be easily connected and disconnected with the grip and driving means.

Other objects, features and advantages of the present invention will become apparent enough by the following explanation.

BRIEF DESCRIPTION OF THE DRAWINGS

FIG. 3 is a general schematic view of a device for diagnosing a body cavity interior with supersonic waves.

DETAILED DESCRIPTION OF THE INVENTION

Figure 1:
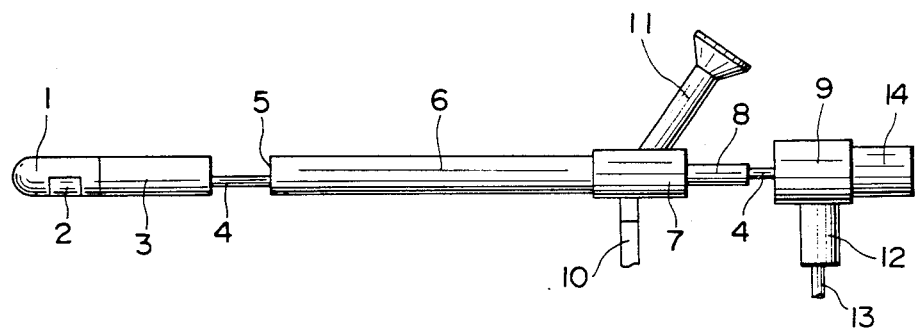
FIG. 1 is an elevation showing a conventional device for diagnosing a body cavity interior with supersonic waves.

Prior to explaining an embodiment of the present invention, a conventional example of a device for diagnosing a body cavity interior with supersonic waves wherein an endoscope for observing a body cavity interior and a supersonic wave probe for obtaining a supersonic wave signal image are combined with each other shall be explained with reference to FIGS. 1 and 2. In these drawings, the reference numeral 1 indicates a supersonic wave probe tip, a window 2 for transmitting and receiving supersonic wave signals is formed in the side part of the tip and a fine diameter shaft 4 is connected to the rear part of the tip through a curved part 3. Cords for transmitting and receiving supersonic waves and wires (not illustrated) for driving a mirror within the above mentioned supersonic wave probe tip 1 are contained in this shaft. This shaft 4 is passed through a channel in an inserted part 6 in which an endoscope 5 is arranged and is connected at the rear end to a driving part 9 through an endoscope hand part 7 and channel inserting port 8. A light guide cable 10 and an eyepiece part 11 inclined to the axial direction of the inserted part 6 are connected to the above mentioned endoscope hand part 7. A holding handle 12 is connected below the driving part 9. A signal cable 13 is inserted through the handle 12. A driving motor 14 is connected to the rear of the driving part 9.

Figure 2:
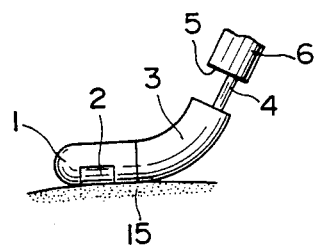
FIG. 2 is an explanatory view of the diagnosing device in FIG. 1 as being used.
Figure 3:
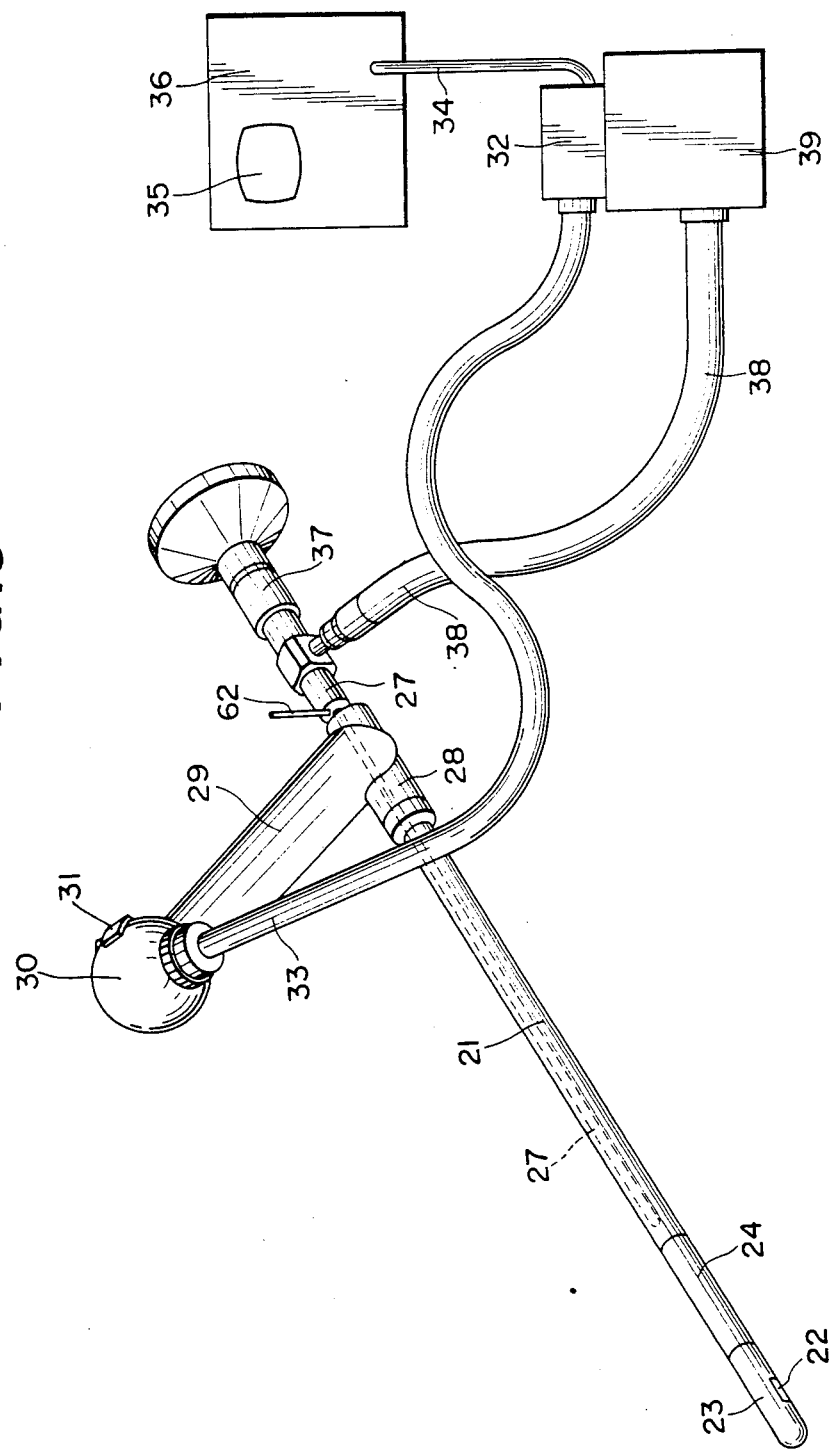
FIG. 3 and others following it show an embodiment of this invention.
Figure 4:
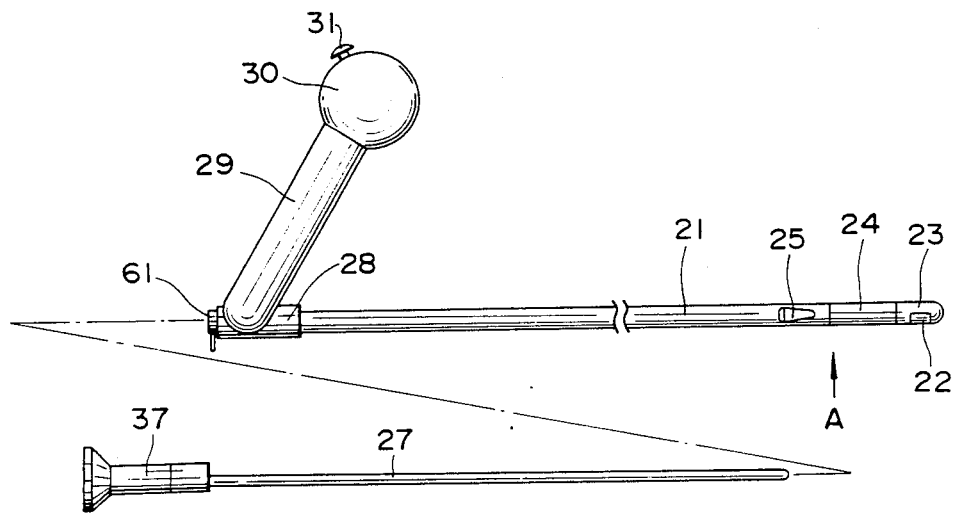
FIG. 4 is an elevation showing an endoscope as pulled out of an inserted part.
Figure 5:
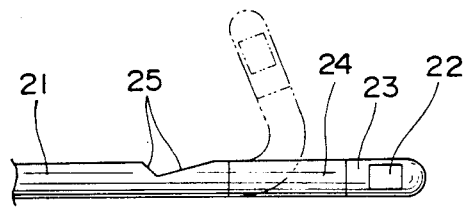
FIG. 5 is a view as seen in the direction indicated by the arrow A in FIG. 4.

In the above mentioned supersonic wave diagnosing device, in order to obtain a supersonic wave image, the inserted part 6 and supersonic wave probe tip 1 are inserted into a body cavity, the supersonic wave probe tip 1 is pushed down in contact with a predetermined internal organ 15 caught within the field of vision of the endoscope 5 within the inserted part 6 and the curved part 3 is curved as shown in FIG. 2 so as to bring the window 2 of the supersonic wave probe tip 1 into contact with the internal organ 15.

However, in the above mentioned formation, there have been inconveniences that, in the operation, the operator must hold the handle 12 of the driving part 9 with the other hand while holding the endoscope hand part 7 with one hand and can not do such other works as, for example, of leading the posture of the patient and pressing the body wall.

Further, the driving part 9 and driving motor 14 are integrally arranged on the handle 12 of the inserted part 6. Therefore, the handle 12 is so heavy that it is hard to insert the inserted part 6 into a body cavity and to make a diagnosing operation. In addition, the volume on the hand side is so large as to interfere with the operation of the device and the observation with the endoscope.

As the signal cable 13 connected to the handle 12 is connected below the handle 12, particularly in case the inserted part 6 is inserted to diagnose an internal organ in the deep, when the inclination of this inserted part 6 is large, the signal cable 13 will contact on the connecting projecting side with the body wall and the operation will become difficult. It is not preferable.

Further, in the above mentioned conventional device, the light guide cable 10 of the endoscope 5 and the signal cable 13 of the driving part 9 are connected respectively to the endoscope 5 and handle 12 in different connecting directions to interfere with such operations as inserting the inserted part 6 into the body cavity, curving the curved part 3 and close contacting the supersonic wave probe tip 1 with an internal organ. It is not preferable.

Therefore, the present invention is made to solve the problems of the above mentioned conventional example and prior arts.

A body cavity interior supersonic wave diagnosing device embodying the present invention shall be explained in the following with reference to FIGS. 3 to 16. In these drawings, the reference numeral 21 indicates an inserted part, a supersonic wave probe tip 23 having a window 22 for transmitting and receiving supersonic waves on the side surface and a curved part 24 are connected in turn from the front to the tip of this inserted part 21 and these inserted parts 21, supersonic wave probe tip 23 and curved part 24 are formed to be of substantially the same diameter. An incised window 25 incised in the direction of the field of vision is formed on the outer periphery of the inserted part 21 in the rear of the above mentioned curved part 24, an endoscope guide tube 26 is arranged from this incised window 25 to the rear end of the inserted part 21 and a perspective endoscope 27 of a fine diameter is telescopically inserted in the guide tube 26. In the illustrated abdomen cavity internal organ diagnosing device, the incised window 25 formed in the inserted part 21 is in the right direction as seen from the operator in the normal using state so that the tip of the perspective endoscope 27 may be positioned in the incised window 25 and the diagonally right front may be within the field of vision of the endoscope. The above mentioned perspective endoscope 27 has a vision field direction of substantially 45 degrees or more. Also, the incised window 25 formed in the inserted part 21 has a vision field direction inclination angle of 5 to 25 degrees so that the field of vision of the endoscope 27 may not be intercepted by the outer periphery of the inserted part 21.

A hand part body 28 is connected to the rear end of the above mentioned inserted part 21. A grip 29 inclined forward by about 60 degrees with the axial direction is integrally connected to the outer periphery of the upper part of this hand part body in the normal using state so as to be gripped with one hand by the operator. The head of this grip 29 has a substantially spherical curved operating part 30 on which a curved operating level 31 projects so as to be operated with the thumb of the hand gripping the above mentioned grip 29.

A driving means unit 32 containing a motor for scanning supersonic waves is formed separately from the above mentioned grip 29. This driving means unit 32 and the grip 29 are connected with each other through a flexible driving cable 33. Further, the driving means unit 32 is connected to an indicating means 36 provided with a Braun tube 35 through a signal cable 34. A flexible light guide cable 38 is connected in front of an eyepiece part 37 of the above mentioned perspective endoscope 27 so as to be connected to a light source means 39. This light guide cable 38 and the above mentioned cable 33 are connected in the same lateral direction respectively with the eyepiece part 37 of the endoscope and the curved operating part 30 of the head of the grip 29. Thus, the operability is improved so as not to interfere with the insertion of the inserted part 21 into the body cavity, the operation of contacting the supersonic wave probe tip 23 with a predetermined internal organ and tthe diagnosing operation with supersonic waves.

Figure 6:
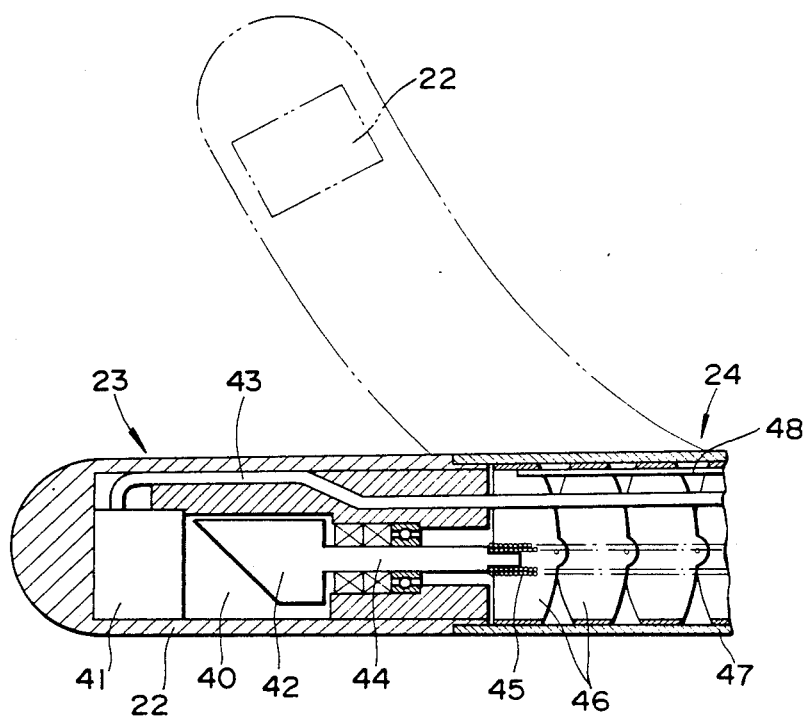
FIG. 6 is a cross-sectional view showing a supersonic wave probe tip and curved part.

The supersonic wave probe tip 23 and curved part 24 are formed as shown in FIG. 6. That is to say, a medium chamber 40 is formed in the supersonic wave probe tip 23. A supersonic wave oscillator 41 and a mirror 42 are arranged as opposed to each other within this chamber 40. A signal cable 43 inserted through the inserted part 21 from the driving means unit 32 is connected to this oscillator 41. A shaft 44 is formed on the mirror 42. A flexible driving shaft 45 is connected to this shaft 44. On the other hand, the curved part 24 is formed by pivoting a plurality of articulated members 46 which are coated with a rubber coating 47. Further, an operating wire 48 inserted through the curved operating part 30 is fixed to the articulated member 46 at the front end.

Figure 12:
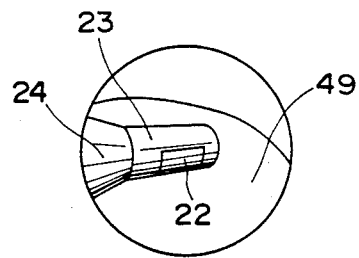
FIG. 12 is an explanatory view showing the field of vision of the endoscope in FIG. 11.

The curved direction of this curved part 24 is set in the direction of the field of vision of the endoscope 27, that is, in the right direction as seen from the operator in the normal using state. Thus the window 22 for transmitting and receiving supersonic waves is within the field of vision of the endoscope 27 as shown in FIG. 12. Thus, in the illustrated device for diagnosing internal organs within the abdomen cavity, the direction of the field of vision of the endoscope 27 inserted in the inserted part 21 and the curved direction of the curved part 24 are set in the right direction as seen from the operator. Thus is because, in the case of using the device to diagnose an internal organ 49 within an abdomen cavity, in what part of the skin there are many blood vessels and in what position the internal organ is located are naturally known, therefore the inserting position and inserting direction are medically known and therefore, if the field of vision is in the right direction in the normal using state and the curved part is curved in the direction of the field of vision, the device will be adapted to such operation and observation as the observation of the internal organ and the close contact of the supersonic wave probe tip 23 with the internal organ. Therefore, it is needless to say that, in the device to be used to diagnose others than internal organs within the abdomen cavity with supersonic waves, the above mentioned direction of the field of vision of the endoscope and curved direction need not be in the right direction. Further, the supersonic wave transmitting and receiving window 22 provided in the supersonic wave probe tip 23 is arranged at right angles with the direction of the field of vision of the endoscope, that is, the curved direction.

Figure 7:
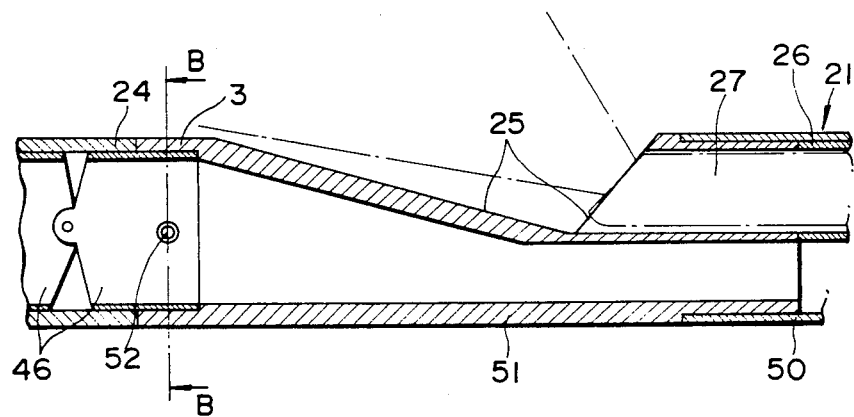
FIG. 7 is a cross-sectional view showing an incised window in the inserted part and a connecting structure of the curved part and a connecting member.
Figure 8:
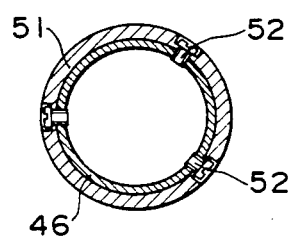
FIG. 8 is a cross-sectional view on line B—B in FIG. 7.
Figure 9:
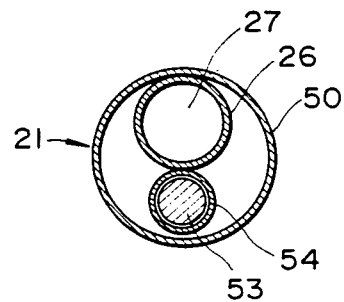
FIG. 9 is a cross-sectioned view of the inserted part.

As shown in FIG. 7, the incised window 25 formed in the inserted part 21 is formed in a connecting member 51 connecting the tip of a jacket tube 50 forming the inserted part 21 and the curved part 24 with each other. This connecting member 51 is fitted and fixed inside the jacket tube 50, and is engaged with the articulated member 46 and is fixed with screws 52 screwed in from the outer periphery outside the connecting member 51, as seen in FIG. 8. By this formation, a wide space can be taken inside the connecting part of the connecting member 51 containing a driving shaft 53, signal cable 43 and operating wire 48 with the articulated member 46. Further, as shown in FIG. 9, in order to enlarge the incised window 25 formed in the above mentioned inserted part 21, the mirror driving shaft 53 inserted through the jacket tube 50 of the inserted part is arranged on the side opposite the direction of the field of vision of the endoscope 27.

Figure 10:
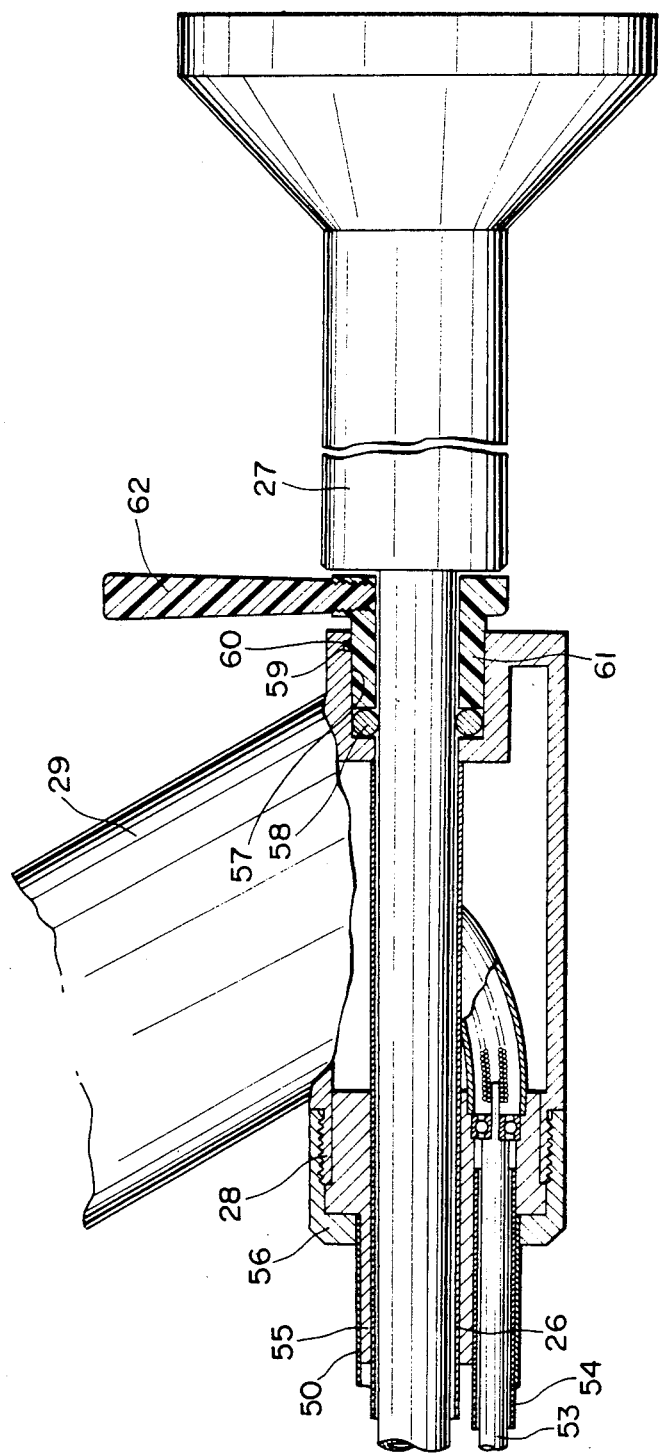
FIG. 10 is a view showing a hand part body with an essential part sectioned.

Further, the connection of the inserted part 21 and hand part body 28 with each other is as shown in FIG. 10. That is to say, a pipe receiver 55 holding and fixing the endoscope guide tube 26, driving shaft tube 54 and inserted part jacket tube 50 is fitted within the hand part body 28. A male screw is formed on the outer periphery of this hand part body 28 and a cap 56 having a female screw is screwed on the male screw from the outer peripheral direction to press and fix the above mentioned pipe receiver 55 to the hand part body 28. Further, the above mentioned mirror driving shaft 53 is borne by bearings within the pipe receiver 55 and ends in the end position of the pipe receiver 55. The flexible driving shaft 45 inserted through the grip 29 connects to this end of the driving shaft 53.

On the other hand, a fixing hole 57 communicating with the endoscope guide tube 26 is formed on the rear end side of the hand body part 28. An O-ring 58 engaging with the outer periphery of the endoscope 27 is inserted in this fixing hole 57. Further, an O-ring fastening body 61 projecting a pin 60 engaged in a spiral groove 59 provided on the inner periphery within the hole 57 is screwed in the above mentioned fixing hole 57 to press and deform the above mentioned O-ring 58. The endoscope 27 is fastened with this deformed O-ring to be fixed in the removing direction and rotating direction and to be kept airtight. The above mentioned fastening body 61 is tubularly formed to accept the insertion of the endoscope 27 and is provided with a lever 62 projecting outwardly on the outer periphery on the rear part.

Figure 13:
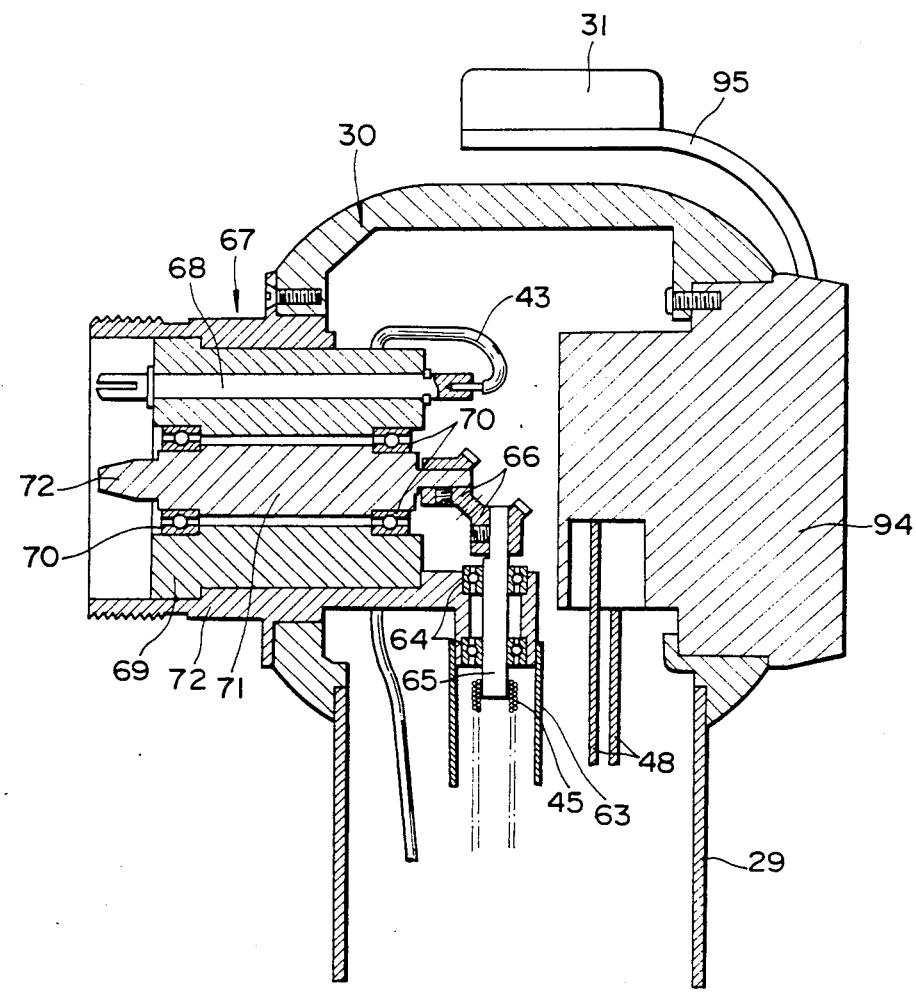
FIG. 13 is a cross-sectional view showing the interior of the operating part.

As shown in FIG. 13, the flexible driving shaft 45 arranged within the above mentioned grip 29 is contained within a flexible tube 63 and is inserted in the axial direction through the grip 29. This flexible driving shaft 45 is connected at the upper end with a shaft 65 borne by bearings 64 on the head side of the grip 29. A bevel gear 66 is pivoted at the upper end of this shaft 65. On the other hand, a connector 67 is formed in the lateral direction in the operating part 30 of the grip head, is borne by bearings 70 within an insulating member 69 through which male side electric connecting pins 68 are inserted, and is provided with a driving shaft joint 71 having the bevel gear 66 and has a male screw formed on the outer periphery of a connector case 72. The driving shaft joint 71 of the above mentioned connector 67 and the shaft 65 are connected at right angles with each other through the bevel gears 66. An engaging projection 72 hexagonal in the section is formed on the connector side of the above mentioned driving shaft joint 71.

Figure 14:
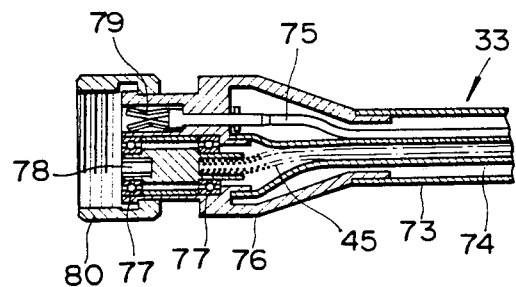
FIG. 14 is a cross-sectional view showing a driving cable on the hand part side.
Figure 15:
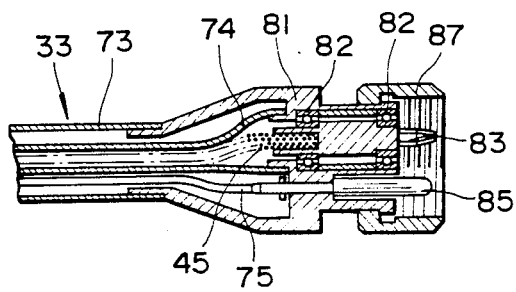
FIG. 15 is a cross-sectional view showing a driving cable on the driving means unit side.
Figure 16:
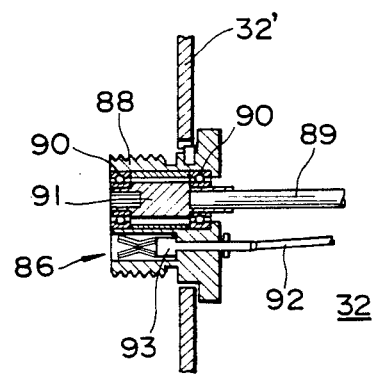
FIG. 16 is a cross-sectional view showing a connector for connecting the driving means unit.

Further, as shown in FIGS. 14 and 15, the cable 33 is provided with a flexible driving shaft 45 inserted through a flexible tube 74, an electric signal cord for the oscillator and rotary detecting signal cords 75 within a flexible jacket tube 73. As shown in FIG. 14, in the connecting part of the connector 67 on the grip side of the cable 33, a case 76 is fixed to the end surface of the jacket tube 73, the above mentioned flexible tube 74 is connected to this case 76 and a driving shaft recess joint 78 borne by bearings 77 and a cord 75 having female side electric connecting pins 79 are arranged. This case is provided rotatably with a connector 67 of the grip 20 so as to be screwed to the connector 67 after the driving shaft engaging part 72 of the connector 67 is engaged with the above mentioned driving shaft recess joint 78. The male side electric connecting pins 68 of the connector 67 are engaged and connected with the female side electric connecting pins 79. Further, as shown in FIG. 15, on the driving means unit 32 side of this cable 33, a case 81 is fixed to the jacket tube 73, the flexible tube 74 is connected to this case 81 and a driving shaft projection (hexagonal in the section) joint 83 borne by bearings 82 and male side electric connecting pins 85 are connected to the cords 75. This case 81 is provided with a rotatable connector connecting screw 87 to be screwed and connected with a connector 86 of the driving means 32 shown in FIG. 16. The connector 86 of the driving means unit 32 shown in FIG. 16 is so formed that a connector case 88 is fitted to a housing 32' and is provided with a driving shaft recess joint 91 connected to a driving shaft 89 connected to a motor through a reduction mechanism or the like and borne by bearings 90 and female side electric connecting pins 93 connected to electric signal cords 92 and has a male screw formed on the outer periphery so as to be screwed with the connector connecting screw 87 of the above mentioned cable 33.

In FIG. 13, the reference numeral 94 indicates a curved operating unit and 95 indicates an operating lever.

Figure 11:
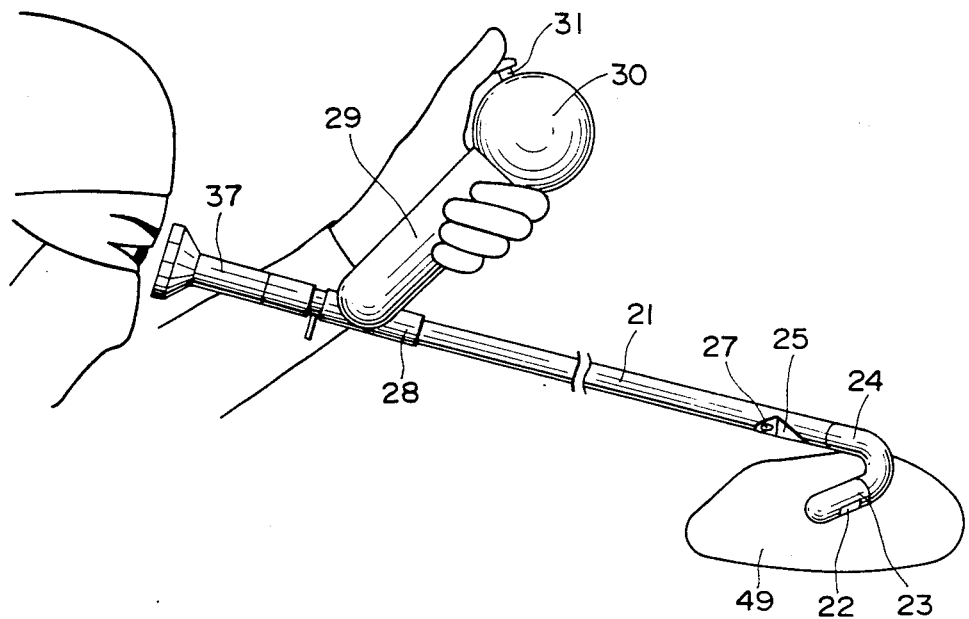
FIG. 11 is an explanatory view showing the device as being used.

In such formation, as shown in FIG. 11, the grip 29 is gripped with one hand by the operator and the inserted part 21 is inserted into a body cavity, for example, an abdomen cavity through a trocar (not illustrated) with the inside of the thumb applied to the curved operating lever 31 of the substantially spherical curved operating part formed in the head of the grip 29. In such case, the supersonic wave probe tip 23 is guided to an internal organ while, for example, the diagonal front in the right direction of the inserted part 21 is being observed with the perspective endoscope 27 through the incised window in the rear of the curved part. After the internal organ 49 is confirmed, the curved operating lever 31 is operated with the above mentioned thumb to pull the operating wire 48 to curve the curved part 24 in the direction of the field of vision of the endoscope 27 or in the right direction as seen from the operator in diagnosing the abdomen cavity interior. The supersonic wave probe tip 23 and window 22 for transmitting and receiving supersonic waves are put into the field of vision and the above mentioned window 22 for transmitting and receiving supersonic waves is brought into close contact with a predetermined part of the internal organ 49 while the internal organ 49 and they are being viewed as shown in FIG. 12.

As the endoscope 27 is made to be in the incised window 25 formed in the inserted part 21 in the rear of the curved part 24 and is perspective at the tip as mentioned above, the supersonic wave probe tip 23 and curved part 28 can be inserted while the internal organ is being sighted without obstructing the field of vision and further, as the supersonic wave probe tip 23 can be curved in the direction of the field of vision of the endoscope 27, the operation of closely contacting the internal organ 49 can be made while both the internal organ 49 and supersonic wave probe tip 23 are being viewed and the internal organ can be accurately and easily diagnosed. Also, the position of window 22 for transmitting and receiving supersonic waves, in contact with the internal organ can be confirmed.

In the present invention, the endoscope 27 is made to be telescopically inserted into the inserted part 21 in the above mentioned embodiment but the optical system may be contained within the inserted part 21.

It is apparent that different working modes can be formed in a wide range without departing from the spirit and scope of the present invention. Therefore, the present invention is not restricted by the specific working mode except by being limited in the appended claims.

We claim:

1. A device for diagnosing a body cavity interior wherein a supersonic wave probe projects supersonic waves directly into a body cavity and has means for transmitting and receiving supersonic waves to diagnose an internal organ or the like within the body cavity with the supersonic waves and an endoscope with means for projecting an illuminating light from a light source means through a flexible light guide into a body cavity to observe the interior of said body cavity, the wave probe and the endoscope form a single unit, comprising:

an elongated body having an insertable tip on one end and a viewing point on the other end thereof;

a hand piece, gripable by the operator, and having a first end attached to said body intermediate said two ends of the body and having a second end angled toward said insertable tip, such that the axis of said hand piece substantially intersects the axis of the elongated body;

a supersonic wave probe tip included in said insertable tip and containing a supersonic wave oscillator and a scanning mirror;

an electric signal cord operatively connected to said probe tip and extending into said hand piece;

a rotary shaft operatively connected with said probe tip and extending into said hand piece;

an endoscope disposed generally axially within said body, and having an eyepiece cooperatively engageable with said body at said viewing point, said endoscope extending to said insertable tip;

driving means separate from said body for driving the oscillator and scanning mirror, said driving means being connected by a flexible cable with said hand piece and operatively connected with said electrical signal cord and said rotary shaft, said flexible cable further having a cable connector at each end thereof, said hand piece having a connector compatible with one of said two cable connectors and said driving means having a connector compatible with the other of said two cable connectors, each connector and cable connector containing connections representing said rotary shaft and said electric signal cord.

2. The diagnosing device of claim 1, wherein the flexible cable connected to said hand piece and the light guide connected to said endoscope extend laterally outward from the same side of the body.

3. The diagnosing device of claim 1, wherein said rotary shaft is flexible within the hand piece and to a point in said body near the entrance of said shaft into said hand piece.

4. The diagnosing device of claim 1, wherein the flexible cable connecting said driving means with said hand piece contains a flexible connecting rotary shaft and connecting electric signal cord therein.

5. The diagnosing device of claim 4, wherein said flexible cable connecting said driving means with said hand piece has a cable connector at each end thereof, said hand piece having a connector compatible with one of said two cable connectors and said driving means having a connector compatible with the other of said two cable connectors, each connector and cable connector containing joints representing said rotary shaft and said electric signal cord.

6. The diagnosing device of claim 1, wherein an incised window is provided in said insertable tip to allow said endoscope to view the organ to be diagnosed.

7. The diagnosing device of claim 6, wherein said probe tip is flexible and may be bent at an angle responsive to control from said hand piece such that said window allows the operator to view the actual operation of said probe tip on the organ to be diagnosed.

* * * * *